United States Patent
Reed et al.

(10) Patent No.: US 7,284,711 B2
(45) Date of Patent: Oct. 23, 2007

(54) CONTAINER AIR FRESHENER UNIT

(75) Inventors: Kenneth A. Reed, Scotch Plains, NJ (US); John C. Crawford, Mahopac, NY (US); Barbara Thomas, Princeton, NJ (US)

(73) Assignee: Colgate-Palmolive Company, New York, NY (US)

( * ) Notice: Subject to any disclaimer, the term of this patent is extended or adjusted under 35 U.S.C. 154(b) by 567 days.

(21) Appl. No.: 10/865,425

(22) Filed: Jun. 10, 2004

(65) Prior Publication Data

US 2005/0274819 A1   Dec. 15, 2005

(51) Int. Cl.
*A24F 25/00* (2006.01)

(52) U.S. Cl. .............. 239/59; 239/57; 239/58; 239/60; 239/289

(58) Field of Classification Search ............ 239/34, 239/57, 58, 59, 60, 289; 222/192
See application file for complete search history.

(56) References Cited

U.S. PATENT DOCUMENTS

| | | | |
|---|---|---|---|
| 759,030 A | 5/1904 | Sheaffer |
| 2,131,975 A | 10/1938 | Samstag |
| 2,657,090 A | 10/1953 | Meek |
| 3,286,872 A | 11/1966 | Burdick, Jr. |
| 3,330,481 A | 7/1967 | Dearling |
| 3,888,416 A | 6/1975 | Lin |
| 3,955,706 A | 5/1976 | Whitaker |
| 4,014,501 A | 3/1977 | Buckenmayer |
| 4,084,732 A | 4/1978 | Dearling |
| 4,200,229 A | 4/1980 | Spector |
| 4,247,042 A | 1/1981 | Schimanski et al. |
| 4,279,350 A | 7/1981 | King |
| 4,306,679 A | 12/1981 | Dusek et al. |
| 4,341,348 A | 7/1982 | Dearling |
| 4,372,490 A | 2/1983 | Le Caire, Jr. |
| 4,382,548 A | 5/1983 | Van Der Heijden et al. |
| 4,549,693 A | 10/1985 | Barlics |
| 4,709,425 A | 12/1987 | Bavaveas et al. |

(Continued)

*Primary Examiner*—Steven J. Ganey
(74) *Attorney, Agent, or Firm*—Michael Wallace, Jr.

(57) ABSTRACT

There is an air freshener unit and a combined container and air freshener unit. The air freshener unit is mounted onto the upper portion of the container and is comprised of a first section and a second section. In one embodiment the first section is a holder for a fragrance material and the second section is a cover for the first section. The second section in a first position covers and substantially seals the first section and in a second position allows air to pass through a space between the first section and the second section and deliver the fragrance material to the atmosphere exterior to the air freshener unit. In a second embodiment both the first section and the second section contain fragrance material. In the first embodiment structure the first section is comprised of a plurality of recesses which hold the fragrance material and the second section is of a conforming shape to cover and substantially seal the plurality of recesses in a first position and in a second position allows air to pass between the first section and the second section to deliver the fragrance to the exterior of the air freshener unit. In a second embodiment structure both the first section and the second section are comprised of a plurality of recesses and deliver the fragrance material in the same manner. The fragrance material is held in the recesses and is in a solid or gel form.

34 Claims, 3 Drawing Sheets

U.S. PATENT DOCUMENTS

| | | |
|---|---|---|
| 4,759,501 A | 7/1988 | Silvenis et al. |
| 4,858,758 A | 8/1989 | Mitchell et al. |
| 5,165,603 A | 11/1992 | Hahn |
| 5,379,917 A | 1/1995 | Brown et al. |
| 5,381,914 A | 1/1995 | Koyama et al. |
| 5,477,640 A * | 12/1995 | Holtkamp, Jr. .............. 239/60 |
| 5,542,557 A | 8/1996 | Koyama et al. |
| 5,595,324 A | 1/1997 | Brown et al. |
| 5,636,787 A | 6/1997 | Gowhari |
| 5,799,826 A | 9/1998 | Brown et al. |
| 6,062,425 A | 5/2000 | Brown et al. |
| 6,394,264 B2 | 5/2002 | Riviello, Jr. |
| 6,511,726 B1 | 1/2003 | Kinigakis |
| 6,569,387 B1 | 5/2003 | Furner et al. |
| 6,729,506 B2 | 5/2004 | Brown et al. |
| 6,769,631 B2 | 8/2004 | Brown |
| 6,857,579 B2 * | 2/2005 | Harris ........................ 239/34 |
| 2002/0030116 A1 | 3/2002 | Brown |

* cited by examiner

CONTAINER AIR FRESHENER UNIT

This invention relates to air freshener units for use on containers. More particularly this invention relates to air freshener units for use on the upper part of containers where such units comprise two sections, one section being a closure for another section.

BACKGROUND OF THE INVENTION

Single purpose air freshener units are used in various forms. These include free standing units, spray units, spray units with an absorbent and those that are plugged into a source of electricity. The function of each is to put a fragrance into a room to replace a foul or stale odor. However, these are all single purpose units. They solely are air freshener units.

It has been known to combine air freshener units with other products. U.S. Pat. No. 3,955,706 discloses an air freshener in combination with a waste container. U.S. Pat. No. 5,636,787 discloses an aromatic dispensing device as a part of eyeglasses. U.S. Pat. No. 2,657,090 discloses a base that can be attached to a container, the base dispensing a volatizable material. U.S. Pat. No. 5,165,603 discloses a container where a fragrance is emitted when the container is in an open orientation. Japanese Utility Model JP-U-58-130441 discloses a flower pot with an aromatic unit in a base stand. And Japanese Utility Model JP-U-60-60300 discloses a vase or ornament with a base stand that has an aromatic unit.

Additional prior art includes U.S. Patent Application 2002/0030116 A1 which discloses various embodiments of air freshener units in combination with a hand lotion dispenser. The air freshener unit can be located at the base or at an upper portion of the hand lotion dispenser.

These are interesting structures for the combination of an air freshener unit with a container. However, they do not disclose a structure where the unit can be opened and closed to control the dispensing of an air freshener fragrance. Further there is no disclosure as to how to use available space on a container for an air freshener unit.

BRIEF DESCRIPTION OF THE INVENTION

The invention comprises an air freshener unit and a container that has an air freshener unit mounted on an upper part of the container. The air freshener unit is comprised of an exterior second section and an inner first section. The first section holds a fragrance material and is covered by a second section. The first section is mounted on the container and in one embodiment is comprised of a plurality of fragrance material holder recesses. The second unit usually provides a conforming cover over the first section and the plurality of fragrance material holder recesses of the first section The second section is relatively moveable with respect to the first section to open and close access of ambient air to the first section which contains up to half or more of the fragrance material.

In one preferred mode the plurality of recesses of the first section preferably are in a stepped arrangement and extend substantially around the container. The second section is of a conforming shape and substantially seals the first section. The closure of the container can be used to hold the first section on the container. The second section is slideably mounted on the first section to open and close the first section and of a structure to remain on the foist section. The first section and the second section can be removed and replaced by removing the container closure and replacing the closure after a new first section and second section unit is placed on the container. In this way the container can be a refillable and reusable container.

In another embodiment the second section also can contain a fragrance in recesses on the inner surface of the second section. In this way more fragrance can be held by the unit and there can be a greater exposed surface area for a more rapid delivery of the fragrance. In this embodiment the fragrance will be in a more solidified form including a gel form.

In order to use the air freshener unit the second section is elevated above the first section. This allows ambient air to pass between the first section and the second section, entrain some of the fragrance from the sections containing the fragrance and exit the air freshener unit at an upper part of the first and second section. The air freshening unit can be closed by moving the second section down over the first section.

The fragrance material can be a solid or a gel. If a solid, it can be a fragrance absorbed into and/or absorbed onto, an absorbent such as a cellulose, silica, alumina or aluminosilicate. Also the fragrance can be contained in or compounded with a plastic material. These materials will be in the recesses of the first section. If a gel, the gel can be cast or liquid hot filled in the recesses of the first or second section. A retaining flange on the first section will keep the second section from being removed from the first and second sections.

DETAILED DESCRIPTION OF THE INVENTION

The air freshener unit and container with an air freshener will be described in more detail in its preferred embodiments with reference to the Figures.

Figure 1:
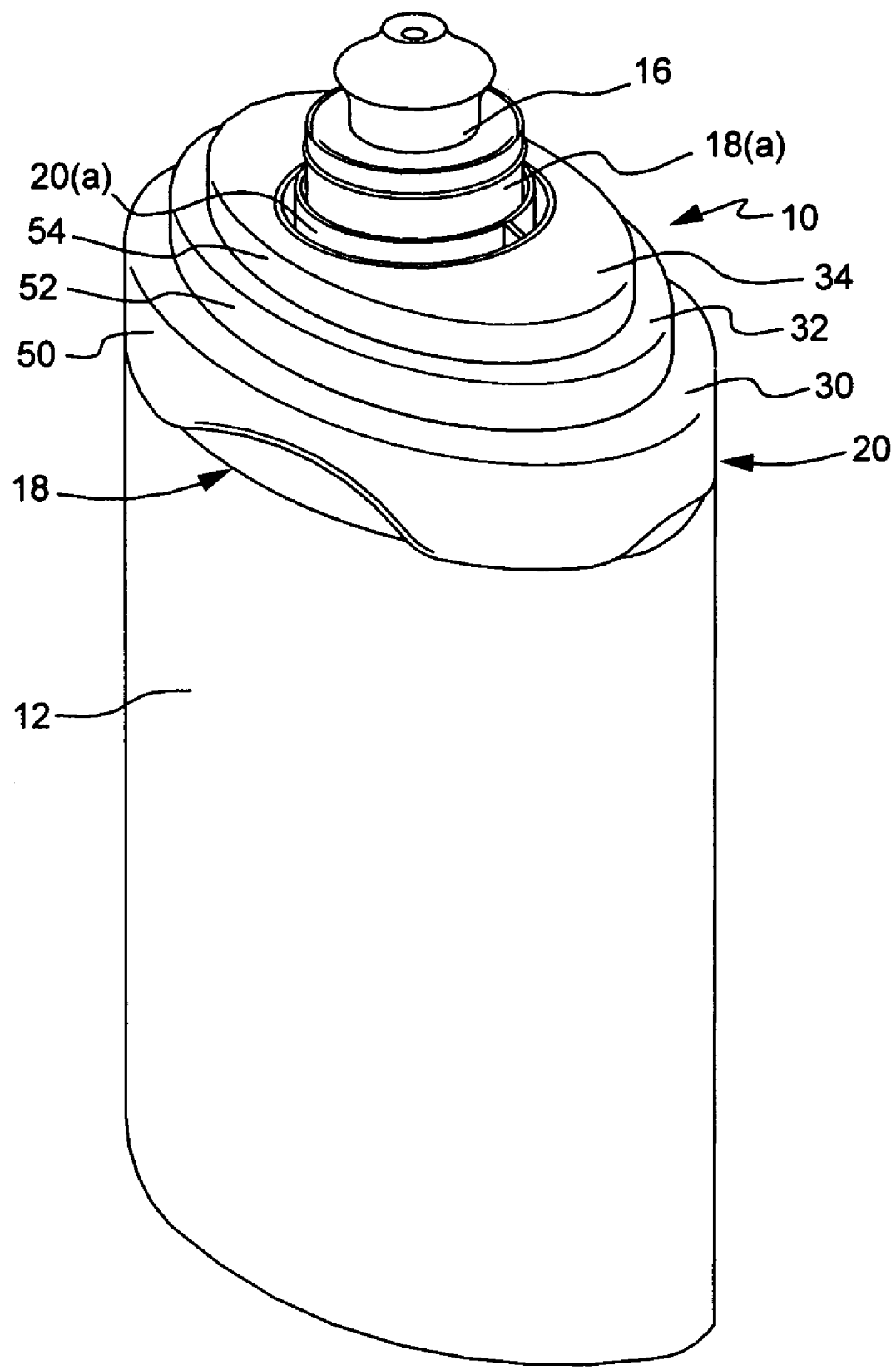
FIG. 1 is a perspective view of a container with the air freshener unit, the air freshener unit being closed.

FIG. 1 shows container 12 and air freshener unit 10. The container has a closure 16 which is shown here to be a common push/pull closure. In this view the outer second section 20 of the air freshener unit is seen. Part of the first section 18 is seen at the lower periphery of the second section 20. The second section 20 which functions as a cover for the first section 18 is shown in a stepped arrangement with substantially vertical surfaces 50, 52, 54 and substantially horizontal surfaces 30, 32, and 34. A first section collar 18(*a*) on the first section is locked into the container 12 by closure 16. The second section collar 20 (*a*) is slideably adjustable on first section collar 18(*a*) to open and close the air freshener unit. Flange 48 (see FIG. 2) on a lower part of first collar 18(*a*) maintains the first section on the container under the closure 16. Flange 38 (see FIG. 2) on an upper part of collar 18(a) in cooperation with protrusion 36 on collar 20(a) maintains second section 20 on first section 18.

Figure 2:
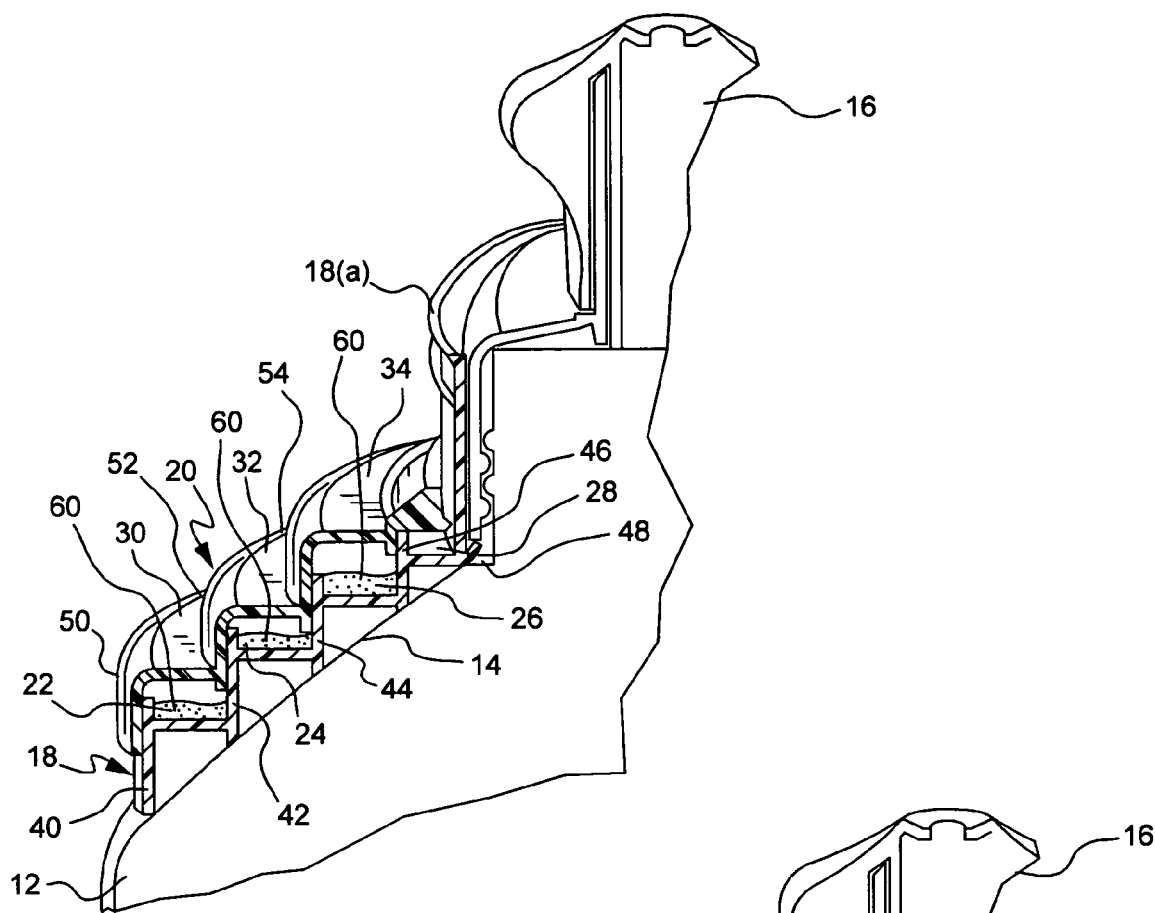
FIG. 2 is a cross-sectional view of the air freshener unit with fragrance material in the first section in a closed position.
Figure 3:
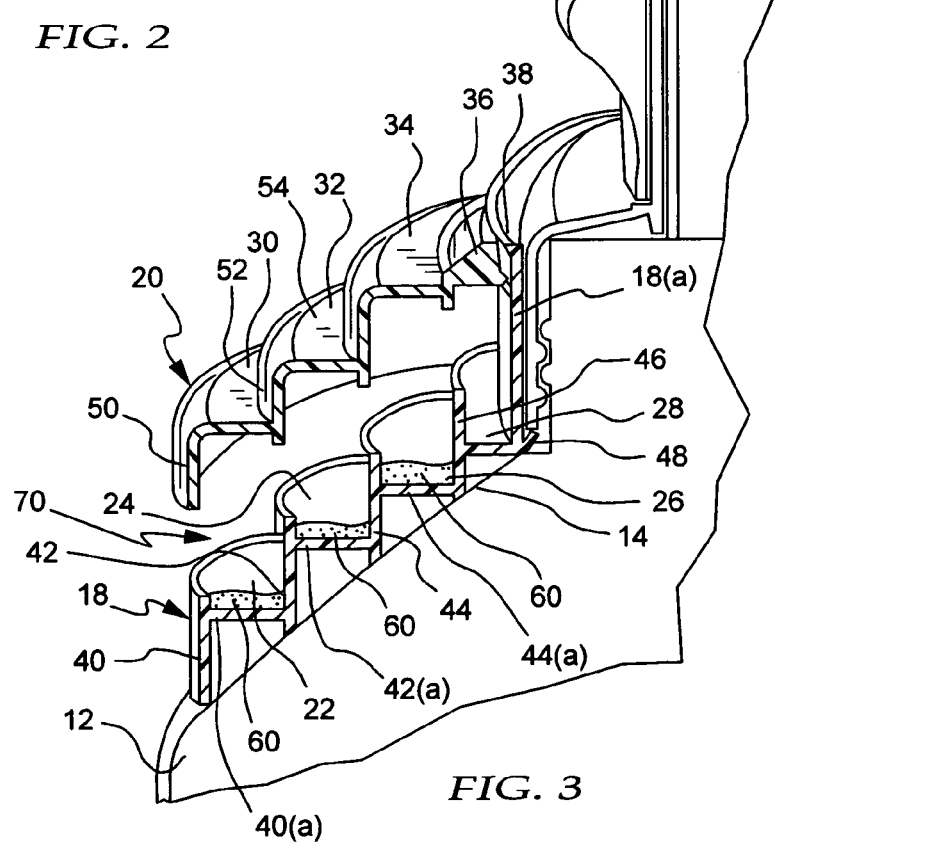
FIG. 3 is a cross-sectional view of the air freshener unit with fragrance material in the first section in an open position.

FIGS. 2 and 3 show the air freshener unit in more detail in a cross-section view where the fragrance material is only in the first section. In FIG. 2 the air freshener unit is closed and in FIG. 3 it is opened. When opened, air 70 can pass between the first section 18 and the second section 20 to entrain some of the fragrance in first section 18 and/or second section 20 and deliver it to the atmosphere. Second section 20 functions as a cover for first section 18.

The first section 18 has three fragrance holder wells 22, 24 and 26. These have substantially vertical walls 40, 42, 44 and 46 with companion substantially horizontal walls 40(a), 42(a) and 44(a) to form the fragrance holder wells. The fragrance holder wells will contain fragrance material 60. The second section 20 which in one embodiment functions as a cover for the first section 18 conforms in general overfitting shape to the first section 18. It is comprised of substantially vertical walls 50, 52 and 54 and substantially horizontal walls 30, 32 and 34. These form a cover or lid for the fragrance holder wells 22, 24 and 26. However in a second embodiment wells that are formed by the vertical walls 50, 52, 56 and horizontal walls 30, 32 and 34 can form fragrance holding wells 80 to also hold fragrance material 60. This can be the same or a different fragrance material. This is shown in more detail in FIGS. 4 and 5. A primary seal of the unit is the close contact of wall 40 of the first unit with wall 50 of the second unit. The close contact of other parts of the first section and the second section will provide secondary sealing. This precludes the passage of entraining air between the sections.

As has been noted the closure 16 holds the air freshener unit on the container. Shown in FIGS. 2 and 3 on second section 20 there is a flange 48 which is held in an interference fit under closure 16. The full air freshener unit can be removed and replaced by the removal of the closure 16. The second section 20 is held onto the first section 18 by interference between projection 36 and flange 38. This latter arrangement limits the travel of the second section on the first section so that the second section will not accidentally be removed from the first section.

Figure 4:
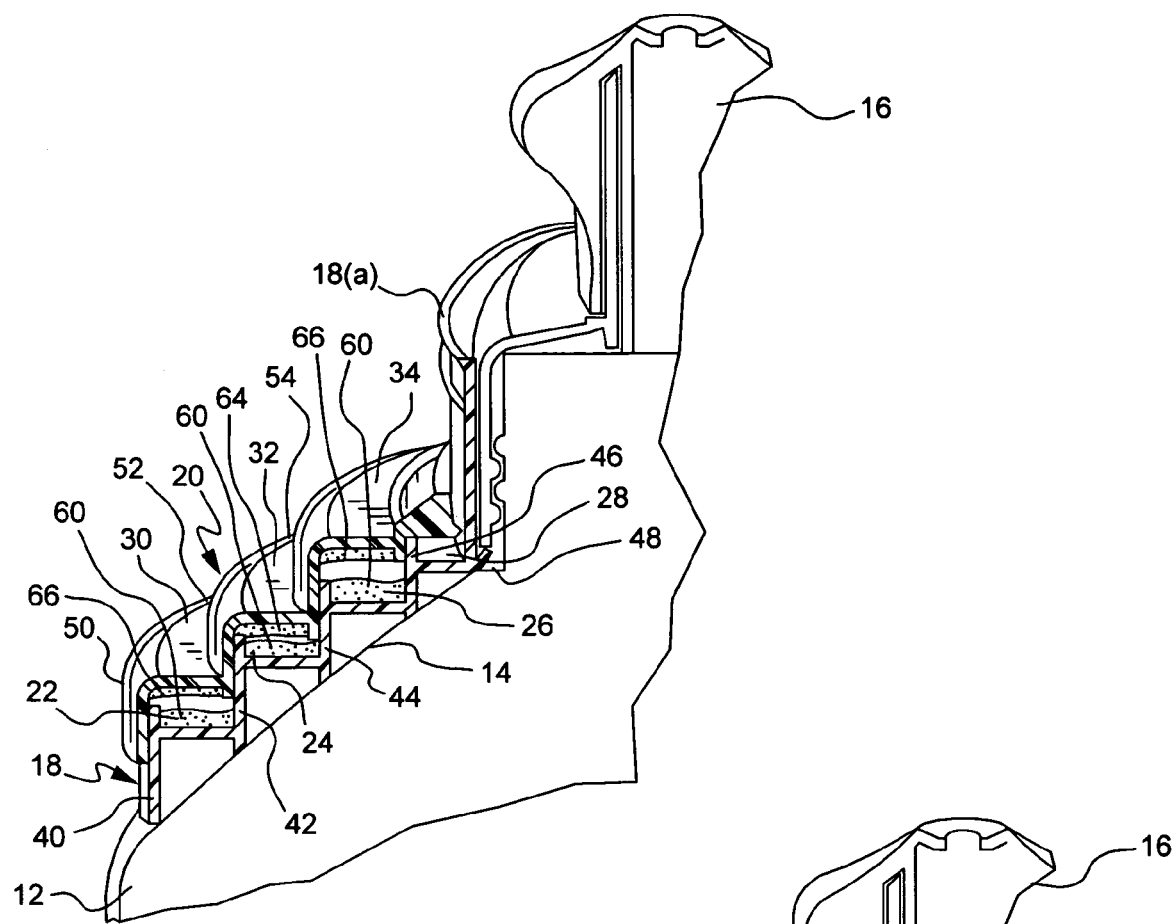
FIG. 4 is a cross-sectional view of the air freshener unit with fragrance material in the first section and the second section in a closed position.
Figure 5:
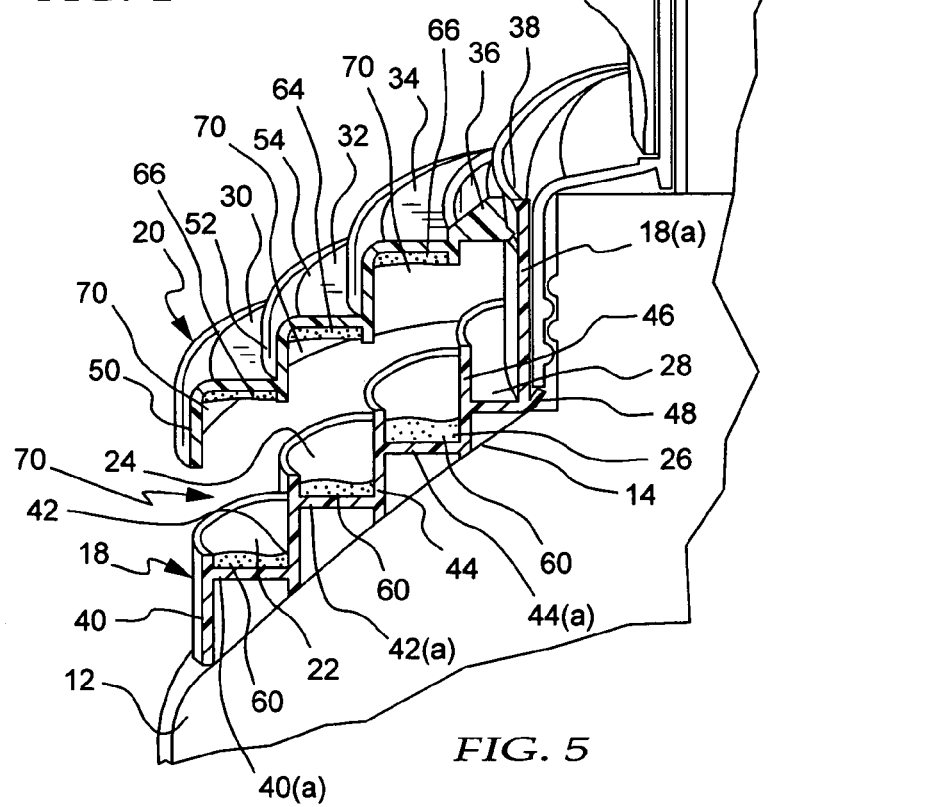
FIG. 5 is a cross-sectional view of the air freshener unit with fragrance material in the first section and the second section in an open position.

FIGS. 4 and 5 show an embodiment of the air freshener where both the first section 18 and the second section 20 contain and deliver fragrance material. The first section 18 and the second section 20 are similar to those of FIGS. 3 and 4 except that in the second section 20 the vertical walls 50, 52 and 54 in conjunction with horizontal walls 30, 32, and 34 form fragrance holding wells 62, 64 and 66. These fragrance holding wells in a similar as the fragrance holding wells of the first section will hold a solid or gel composition that is molded or cast into the holding wells 62, 64 and 66. This embodiment will provide a greater fragrance containing surface area for a more rapid fragrance delivery during use.

In one mode of use the container holds dish washing detergent and will usually be near the sink in a kitchen. Detergent is dispensed via the push/pull closure 16. The fragrance from the fragrance material 60 will be dispensed into the kitchen air by elevating second section 20 above first section 18 as shown in FIG. 3. One function of projection 36 against wall 20 (a) is to hold the second section 20 in relation to the first section 18 at any level. This will control the amount of air that flows through the unit and thus the amount of fragrance delivered to a room. However the fragrance containing and dispensing unit van be used in conjunction with other containers.

The fragrance can be absorbed onto an organic or inorganic solid or can be in a gel form. Solids upon which fragrances can be absorbed include celluloses, silicas, aluminas and aluminosilicates. Fragrances also can be held within organic substances such as ethylene vinyl acetate and ethylene vinyl alcohol. Suitable gels are the polyethylene and polyamide gels. Some such organic substances are available from Arizona Chemical Company, and from International Flavors and Fragrances in its UNICLEAR and POLYIFF lines of products. They also are available from Honeyware under the SYLVACLEAR product line. The fragrance also can be compounded with and contained in plastic materials such as polyethylene, polypropylene and ethylene vinyl acetate. The entraining material will contain from about 20% up to about 90% of fragrance. There is no limitation on the form or composition of the fragrance with the only specifications being that it be held in the fragrance holding wells and that it be deliverable from the second section 20 being raised above the first section 18.

The first section 18 and the second section 20 can be formed from any thermoplastic. This usually will be by injection molding. The useful plastics include the polyethylenes, polypropylenes, ethylene/propylene copolymers, polymers and copolymers of other alkenes, polyethylene terephthalate, polyvinyl chloride, and alkyl butyl styrene polymers.

The invention claimed is:

1. A container with an air freshener unit, said air freshener unit mounted on an upper portion of said container and comprising a first section and a second section, said first section mounted onto said container upper portion and comprising a holder having a plurality of recesses to hold a fragrance material, the second section overlaying said first section and in a first position substantially closing said fragrance material holder from an exterior atmosphere and in a second position allowing said exterior atmosphere to flow between said first section and said second section and to entrain a fragrance at least from said first section to the atmosphere exterior to said air freshener unit.

2. A container with an air freshener unit as in claim 1 wherein said first section conforms to the shape of the upper portion of said container.

3. A container with an air freshener unit as in claim 1 wherein said plurality of recesses form wells to hold said fragrance material.

4. A container with an air freshener unit as in claim 1 wherein a closure for said container maintains said first section of said air freshener unit on said container.

5. A container with an air freshener unit as in claim 1 wherein said second section has a plurality of portions conforming to said first section plurality of recesses, each conforming portion covers a recess of said first section plurality of recesses and assists in sealing the fragrance material of each such first section recess from the atmosphere until said second section is separated from said first section.

6. A container and air freshener unit as in claim 1 wherein said second section is comprised of a plurality of recesses.

7. A container with an air freshener unit as in claim 1 wherein said first section plurality of recesses are in a stepped arrangement.

8. A container with an air freshener unit as in claim 1 wherein said first section plurality of recesses extend substantially around the container.

9. A container with an air freshener as in claim 1 wherein said second section contains a fragrance material.

10. A container with an air freshener unit as in claim 9 wherein a second section holder for fragrance material is a second section plurality of recesses.

11. A container with an air freshener unit as in claim 10 wherein said second section plurality of recesses are in a stepped arrangement.

12. A container with an air freshener unit as in claim 1 wherein said second section is comprised of a plurality of recesses, the second section plurality of recesses overlaying the first section plurality of recesses.

13. A container with an air freshener unit as in claim 1 wherein said fragrance material is one of a solid or a gel.

14. A container with an air freshener unit as in claim 1 wherein an underside of said second section comprises a holder for fragrance material.

15. A container with an air freshener unit as in claim 14 wherein said second section holder of fragrance has a plurality of recesses.

16. A container with an air freshener unit as in claim 15 wherein said first section and said second section plurality of recesses are in a stepped arrangement.

17. A container with an air freshener unit as in claim 1 wherein said second section has a plurality of recesses, the first section plurality of recesses which form the holder for said fragrance material in said first section and the plurality of recesses of said second section conform to form a holder for fragrance material in said second section, each conforming second section recess covers a recess of said plurality of recesses of said first section and assists in sealing the fragrance material of each the recesses of the first section and the second section from the atmosphere when said first section and said second section are in a close position.

18. A container with an air freshener unit as in claim 17 wherein said plurality of recesses of said first section and of said second section are both in a stepped arrangement.

19. An air freshener unit as in claim 17 wherein said first section plurality recesses and said second section plurality of recesses form opposite facing wells to hold said fragrance material.

20. An air freshener unit as in claim 17 wherein said fragrance material is one of a solid or of a gel.

21. An air freshener unit comprising a first section and a second section, said first section mounted onto said container upper portion and comprising a holder having a plurality of recesses to hold a fragrance material, the second section overlaying said first section and in a first position substantially closing said fragrance material holder from an exterior atmosphere and in a second position allowing said exterior atmosphere to flow between said first section and said second section and to entrain a fragrance at least from said first section to the atmosphere exterior to said air freshener unit.

22. An air freshener unit as in claim 21 wherein said plurality of recesses form wells to hold said fragrance material.

23. An air freshener unit as in claim 21 wherein said second section has a plurality of portions conforming to said first section plurality of recesses, each conforming portion covers a recess of said first section plurality of recesses and assists in sealing the fragrance material of each such first section recess from the atmosphere until said second section is separated from said first section.

24. An air freshener unit as in claim 21 wherein said second section is comprised of a plurality of recesses.

25. An air freshener unit as in claim 21 wherein said first section plurality of recesses are in a stepped arrangement.

26. An air freshener unit as in claim 21 wherein said first section plurality of recesses extend substantially around the container.

27. An air freshener as in claim 21 wherein said second section contains a fragrance material.

28. An air freshener unit as in claim 27 wherein said second section holder for fragrance material is comprised of a second section plurality of recesses.

29. An air freshener unit as in claim 28 wherein said second section plurality of recesses are in a stepped arrangement.

30. An air freshener unit as in claim 21 wherein said second section is comprised of a plurality of recesses, the second section plurality of recesses overlaying the first section plurality of recesses.

31. An air freshener unit as in claim 21 wherein said fragrance material is one of a solid or a gel.

32. Air freshener unit as in claim 21 wherein an underside of said second section further comprises a holder for fragrance material.

33. An air freshener unit as in claim 32 wherein said second section holder of fragrance material has a plurality of recesses.

34. An air freshener unit as in claim 33 wherein said first section and said second section plurality of recesses are in a stepped arrangement.

* * * * *